United States Patent [19]

Cunningham et al.

[11] 4,319,060
[45] Mar. 9, 1982

[54] PROCESS FOR PRODUCING 1,2-DICHLORO-1,1,2,2-TETRAFLUOROETHANE SUBSTANTIALLY FREE OF 1,1-DICHLORO-1,2,2,2-TETRAFLUOROETHANE

[75] Inventors: William J. Cunningham, Williamsville; Addison M. Smith, Buffalo; Robert A. Wiles, Hamburg, all of N.Y.

[73] Assignee: Allied Chemical Corporation, Morris Township, Morris County, N.J.

[21] Appl. No.: 214,079

[22] Filed: Dec. 8, 1980

[51] Int. Cl.$^3$ .............................................. C07C 17/38
[52] U.S. Cl. .................................... 570/177; 570/134
[58] Field of Search ............... 570/134, 163, 170, 177

[56] References Cited

U.S. PATENT DOCUMENTS 2,661,377 12/1953 McKenna et al. ................. 570/163

FOREIGN PATENT DOCUMENTS 1161249  1/1964  Fed. Rep. of Germany ...... 570/177
2822471 12/1978  Fed. Rep. of Germany .
1453510 10/1966  France ............................... 570/177

Primary Examiner—Thomas A. Waltz
Attorney, Agent, or Firm—Jay P. Friedenson

[57] ABSTRACT

The present invention provides a novel process for producing 1,2-dichloro-1,1,2,2-tetrafluoroethane substantially free of the 1,1-isomer. The process includes contacting, in the vapor phase, an organic feed composition containing a major amount of the 1,2-isomer and a minor amount of 1,1-isomer with hydrogen in the presence of a hydrodechlorination catalyst. The process selectively degrades the 1,1-isomer. Also provided is a process for producing high purity 1,2-isomer.

12 Claims, No Drawings

PROCESS FOR PRODUCING 1,2-DICHLORO-1,1,2,2-TETRAFLUOROETHANE SUBSTANTIALLY FREE OF 1,1-DICHLORO-1,2,2,2-TETRAFLUOROETHANE

TECHNICAL FIELD

This invention relates to the field of fluorocarbons. More specifically, it relates to a process of purifying a particular fluorocarbon.

BACKGROUND ART

The purification of 1,2-dichloro-1,1,2,2-tetrafluoroethane is known in the prior art, as illustrated by Belgian Pat. No. 685,511. In this type of prior art, the content of 1,2-dichlorotetrafluoroethane in a mixture of the 1,1- and 1,2- compounds is increased by passing the mixture as a liquid or gas at 50°–500° C. over a halogen-exchange catalyst, preferably activated carbon or alumina. The life of the catalyst can be enhanced by conducting the reaction in the presence of HF or $Cl_2$. This patent discloses that the 1,1-isomer is significantly less stable at room temperature than the 1,2-isomer, especially toward hydrolysis. This type of prior art does not contact the isomer mixture with hydrogen in the presence of a catalyst. Furthermore, in Example 1 of the Belgian patent, a very high contact time of 48 hours is used. A further deficiency of this type of prior art is that it may not be capable of producing the 1,2-isomer substantially free of the 1,1-isomer. In this regard, the best example of the Belgian patent shows increase of 1,2-isomer from 92 to 98%.

It is also known in the prior art to react a mixture of 1,2-dichloro-1,1,2,2-tetrafluoroethane, and 1,1-dichloro-1,2,2,2-tetrafluoroethane with hydrogen at a high temperature in the presence of a hydrogenation catalyst. This type of process is illustrated by German Offenlegungsschrift No. 2,822,471, which was laid open on Dec. 7, 1978. A counterpart of this publication is Belgian Pat. No. 867,285 which is cited in Chemical Abstracts 90:151557w. This type of prior art process is used to produce tetrafluoroethane from dichlorotetrafluoroethane. The German publication uses temperatures as low as 240° C., and contact times of about 10 seconds for temperatures ranging from 295° to 420° C. Palladium on carbon is disclosed as a catalyst useful in that process with 2 to 5 weight percent palladium being on the carbon substrate. The proportion of hydrogen used varies, with Example 1 thereof showing a 2:1 molar ratio of hydrogen to organic feed material.

In none of this art and in none of the prior art of which we are aware, is there a process for producing 1,2-dichloro-1,1,2,2-tetrafluoroethane substantially free of the 1,1-isomer. Also, in none of this art is there a process requiring a very short contact time for producing the 1,2-isomer substantially free of the 1,1-isomer.

SUMMARY OF THE INVENTION

It is accordingly one object of the present invention to provide a process for producing 1,2-dichloro-1,1,2,2-tetrafluoroethane substantially free of the 1,1-isomer.

A further object is to provide a process requiring a very short contact time for producing the 1,2-isomer substantially free of the 1,1-isomer.

Additional objects, advantages, and novel features of the invention will be set forth in the description which follows, and in part, will become apparent to those skilled in the art upon examination of the following, or may be learned by practice of the invention. The objects and advantages of the invention may be realized and attained by means of instrumentalities and combinations particularly pointed out in the appended claims.

To achieve the foregoing objects and in accordance with the purpose of the invention, as embodied and broadly described herein, the present invention is directed to a process for producing 1,2-dichloro-1,1,2,2-tetrafluoroethane substantially free of the 1,1-isomer. This process includes the step of contacting, in the vapor phase, an organic feed composition containing a major amount of 1,2-dichloro-1,1,2,2-tetrafluoroethane and a minor amount of 1,1-dichloro-1,2,2,2-tetrafluoroethane with hydrogen in the presence of a hydrodechlorination catalyst for a selected time ranging from about 2 to 6 seconds. The proportion of hydrogen ranges from an amount at least slightly in excess on a molar basis, of the concentration of the 1,1-isomer in the organic feed composition, to an amount about substantially equimolar to the organic feed composition. The contacting is carried out at a selected temperature suitable for the hydrodechlorination catalyst selected. As a result of the process, substantially all 1,1-isomer is selectively degraded so as to provide 1,2-isomer substantially free of 1,1-isomer, as a product. Also provided is a process for producing high purity 1,2-isomer from this product. This process comprises distilling this product to separate high purity 1,2-isomer therefrom.

BEST MODE FOR CARRYING OUT THE INVENTION

As explained above, in accordance with the invention, there is provided a process for producing 1,2-dichloro-1,1,2,2-tetrafluoroethane, which is hereinafter called R-114, substantially free of 1,1-dichloro-1,2,2,2-tetrafluoroethane, which is hereinafter called R-114a. As the starting material for this process, there is used an organic mixture containing a major amount of R-114 and a minor amount of R-114a. By a major amount is meant from about 75 up to less than 100 weight percent, and by a minor amount is meant from about 0.1 to 25 weight percent. Commercially produced R-114 generally contains up to 8–10 weight percent R-114a. The commercially produced material is conveniently used as the organic mixture. A particularly convenient starting material contains about 3–4 weight percent R-114a and about 96–97 weight percent R-114.

The process comprises, in accordance with the invention, contacting the organic mixture containing R-114 and R-114a with hydrogen in the presence of a hydrodechlorination catalyst. The contacting is carried out in the vapor phase. The proportion of hydrogen is believed to be a critical feature of the invention. As a minimum amount, the hydrogen is at least slightly in excess, on a molar basis, of the concentration of R-114a in the organic feed material. As an upper limit, the hydrogen is present in an amount that is about substantially equal, on a molar basis, to the feed material, that is, about 1:1. Use of hydrogen in an amount that is at the lower end of the range described may be especially useful since reactor capacity may be improved.

A hydrodechlorination catalyst in accordance with the invention is suitably a metal such as nickel, copper or iron in combination with a support such as carbon, $CaF_2$, $MgF_2$ and $AlF_3$. When a catalyst of this type is used, the contacting step is carried out at a temperature in the range of about 400°–550° C., with the temperature preferably being in the range of about 400°–500° C. Preferably, the catalyst is a noble metal catalyst. Advantageously, this catalyst contains a noble metal such as platinum, ruthenium, rhodium, palladium, osmium and iridium, and contains a support such as $Al_2O_3$, $AlF_3$ and carbon. When a noble metal catalyst is used, the contacting step is carried out at a temperature ranging from about 100°–300° C., with a temperature of about 250°–275° C. being preferred. A preferred noble metal catalyst is about 0.25–0.75% palladium on carbon, with about 0.5% palladium on carbon being especially preferred.

Another critical feature of the invention is believed to be the time of the contacting step. This time ranges from about 2–6 seconds. A particularly convenient time for the contacting step is about 5 seconds. We believed that control of the hydrogen to organic material mole ratio and control of the contact time, as described above, is primarily responsible for the selective degradation of R-114a characterizing this invention. Also, we believe that, in the case of palladium on carbon catalyst, for example, that the use of a small amount of palladium such as about 0.25–0.75%, could contribute to the selectivity discovered by us.

The contacting step is carried out in a suitable reactor such as a one-inch I.D. × 30-inch long stainless steel pipe lined with Coors 998 high purity fused alumina having a ¾ inch I.D. Temperature control is conveniently obtained using a ¼ inch O.D. alumina thermowell that runs the length of the reactor. The reactor is contained in a 24-inch long electrically wound tube furnace.

In carrying out the process, hydrogen and the organic feed material are metered into the bottom of the reactor. The flow rate to be used for the hydrogen and the organic feed material depends upon the amount of catalyst used. Thus, the more catalyst used, the greater the flow rate, whereas the less catalyst used, the lower the flow rate. Illustratively, the flow rate is about 1.23 moles per hour.

The reaction products exiting from the reactor are scrubbed with caustic to remove by-product HCl. The scrubbed organic vapors are then dried over a drying agent such as Drierite ® and condensed in a trap such as a liquid nitrogen cooled trap. Unreacted hydrogen passes through the trap and is vented.

Prior to carrying out the contacting step, the catalyst may be preconditioned. Preconditioning is achieved by heating the catalyst to an appropriate temperature and pretreating with hydrogen for an appropriate time. The temperature and time required for preconditioning depends upon the catalyst undergoing this treatment. Preconditioning produces a catalyst that is fully active. In the case of a palladium catalyst, preconditioning is carried out by heating the catalyst such as palladium on carbon to a temperature of about 320° C. and treating with hydrogen for about four hours. As a result, palladium salts such as the oxide and chloride are reduced to provide free palladium metal on the carbon. Preconditioning is not necessary since during the contacting step, the catalyst is reduced by the hydrogen present and therefore becomes fully active.

In a preferred embodiment of our process, the organic feed material contains about 3–4 weight percent R-114a and about 96–97 weight percent R-114, the contacting time is about 5 seconds, and the hydrogen is present in an amount that is substantially equimolar to the organic feed mixture. In this embodiment, the catalyst is about 0.5% palladium on carbon, and the contacting step is carried out at a selected temperature ranging from about 250°–275° C.

As a result of the process, substantially all R-114a is selectively degraded as to provide R-114 substantially free of R-114a, as a product. The degradation reactions during the contacting step are believed as follows:

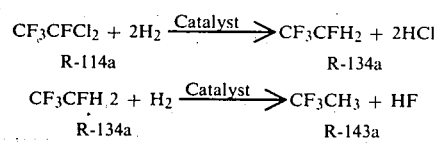

In addition to the degradation scheme for R-114a set forth above, an analogous reaction scheme is believed to occur with R-114 but only to a very minor extent so as to produce R-134. Thus, our process is substantially based upon the discovery that under the reaction conditions described, R-114a reacts much faster than R-114 with hydrogen. For illustration purposes, when a mixture containing about 3–4 weight percent R-114a and about 96–97 weight percent R-114 is used as the organic feed material, only about 1% of the R-114 is degraded to form R-134, whereas substantially all the R-114a is degraded.

In another embodiment of our invention, we provide a process for producing high purity R-114 from the product mixture produced by the process just described. This product mixture contains R-114, R-134a, R-134, and R-143a. This process comprises distilling this product mixture using conventional distillation procedures to separate high purity R-114 from the other reaction products. Azeotropes may be encountered when distilling the product mix, with a R-143a/R-134a azeotrope (possibly 2/1) having been identified.

As can be seen from the above description, by our process, R-114a is selectively degraded with very little degradation of R-114 so as to produce R-114 substantially free of R-114a.

The below example is illustrative of the invention. It is to be understood that this example is not in any way to be interpreted as limiting the scope of the invention. Rather, it is intended that the scope of the invention be defined by the claims appended hereto.

EXAMPLE

To the reactor described above, contained in a 24 inch long, electrically wound tube furnace, 160 ml (80.7 g) of granular 0.5% Pd on carbon, obtained from Engelhard Industries, was charged. The catalyst was preconditioned by heating to 320° C. and treatment with hydrogen for about four hours. The reactor was then cooled to a temperature of about 260° C. An organic feed material containing 3–4 weight percent R-114a and 96–97 weight percent R-114 was metered into the bottom of the reactor at a rate of 1.23 moles per hour. Hydrogen was fed at this same rate to the reactor. The contact time was 5 seconds. Over a period of 10 hours, approximately 2,200 g of the organic feed material was fed into the reactor. The reaction products were scrubbed with caustic to remove HCl, and the scrubbed organic vapors were dried over Drierite ®. The dried vapors were condensed in a liquid nitrogen cooled trap, and unreacted hydrogen passed through the trap and was vented. By gas chromatography, it was determined that the reaction product contained 95.68 weight percent R-114, 2.54 weight percent R-134a, 0.99 weight percent R-134, and 0.80 weight percent R-143a. Infrared analysis of the R-114 gas chromatography peak showed not any R-114a to be present.

INDUSTRIAL APPLICABILITY

The process of this invention is useful for selectively degrading R-114a in the presence of R-114 so as to thereby produce R-114 substantially free of R-114a. Also, the present invention provides for the production of high purity R-114.

We claim:

1. A process for producing 1,2-dichloro-1,1,2,2-tetrafluoroethane substantially free of 1,1-dichloro-1,2,2,2-tetrafluoroethane from a mixture comprising 1,2-dichloro-1,1,2,2-tetrafluoroethane and 1,1-dichloro-1,2,2,2-tetrafluoroethane, said process comprising contacting, in the vapor phase, a feed composition comprising a major amount of 1,2-dichloro-1,1,2,2-tetrafluoroethane and a minor amount of 1,1-dichloro-1,2,2,2-tetrafluoroethane with hydrogen in the presence of a hydrodechlorination catalyst for a selected time ranging from about 2-6 seconds; the proportion of hydrogen ranging from an amount at least slightly in excess, on a molar basis, of the concentration of 1,1-dichloro-1,2,2,2-tetrafluoroethane in said feed composition, to an amount about substantially equimolar to said feed composition; said contacting being carried out at a selected temperature suitable for the hydrodechlorination catalyst; whereby substantially all 1,1-dichloro-1,2,2,2-tetrafluoroethane is selectively degraded so as to provide 1,2-dichloro-1,1,2,2-tetrafluoroethane substantially free of 1,1-dichloro-1,2,2,2-tetrafluoroethane, as a product.

2. The process of claim 1, wherein said selected temperature is in the range of about 100°-300° C. when said catalyst is a noble metal catalyst, and wherein said selected temperature is in the range of about 400°-550° C. when said catalyst comprises a support selected from the group consisting of carbon, $CaF_2$, $MgF_2$ and $AlF_3$, and further comprises a metal selected from the group consisting of nickel, copper and iron.

3. The process of claim 2, wherein said catalyst is said noble metal catalyst, which comprises a support selected from the group consisting of $Al_2O_3$, $AlF_3$ and carbon, and further comprises a noble metal selected from the group consisting of platinum, ruthenium, rhodium, palladium, osmium and iridium.

4. The process of claim 3, wherein said selected temperature ranges from about 250°-275° C.

5. The process of claim 4, wherein said noble metal catalyst is about 0.25-0.75% palladium on carbon.

6. The process of claim 5, wherein said noble metal catalyst is about 0.5% palladium on carbon.

7. The process of claim 1, wherein the contacting time is about 5 seconds.

8. The process of claim 1, wherein said hydrogen is present in an amount slightly in excess, on a molar basis, of the concentration of 1,1-dichloro-1,2,2,2-tetrafluoroethane in said feed composition.

9. The process of claim 1, wherein said feed composition comprises about 1-10 weight percent 1,1-dichloro-1,2,2,2-tetrafluoroethane and about 90-99 weight percent 1,2-dichloro-1,1,2,2-tetrafluoroethane.

10. The process of claim 9, wherein said feed composition comprises about 3-4 weight percent 1,1-dichloro-1,2,2,2-tetrafluoroethane and about 96-97 weight percent 1,2-dichloro-1,1,2,2-tetrafluoroethane.

11. The process of claim 6, wherein the contacting is carried out for about 5 seconds, wherein the feed composition comprises about 3-4 weight percent 1,1-dichloro-1,2,2,2-tetrafluoroethane and about 96-97 weight percent 1,2-dichloro-1,1,2,2-tetrafluoroethane and wherein said hydrogen and said feed composition are present in a substantially equimolar amount.

12. A process for producing high purity 1,2-dichloro-1,1,2,2-tetrafluoroethane from the product of claim 1, said process comprising distilling said product to separate high purity 1,2-dichloro-1,1,2,2-tetrafluoroethane therefrom.

* * * * *